(12) United States Patent
Ferguson et al.

(10) Patent No.: US 6,875,179 B2
(45) Date of Patent: Apr. 5, 2005

(54) ULTRASONIC GUIDED CATHETER DEPLOYMENT SYSTEM

(75) Inventors: Scott L. Ferguson, Vilonia, AR (US); Gal Shafirstein, Little Rock, AR (US); Milton Waner, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 49 days.

(21) Appl. No.: 10/453,742

(22) Filed: Jun. 3, 2003

(65) Prior Publication Data

US 2003/0233046 A1 Dec. 18, 2003

Related U.S. Application Data

(60) Provisional application No. 60/389,432, filed on Jun. 17, 2002.

(51) Int. Cl.[7] ................................................. A61B 8/00
(52) U.S. Cl. ..................................................... 600/461
(58) Field of Search ................................ 600/443, 449, 600/461, 566–568

(56) References Cited

U.S. PATENT DOCUMENTS

| | | | | |
|---|---|---|---|---|
| 4,601,292 A | * | 7/1986 | Fidel et al. .................. | 600/453 |
| 5,095,910 A | * | 3/1992 | Powers ........................ | 600/461 |
| 5,199,431 A | | 4/1993 | Kittrell et al. | |
| 5,397,323 A | * | 3/1995 | Taylor et al. ............... | 606/130 |
| 5,398,690 A | * | 3/1995 | Batten et al. ............... | 600/461 |
| 5,700,273 A | | 12/1997 | Buelna et al. | |
| 5,829,439 A | * | 11/1998 | Yokosawa et al. .......... | 600/461 |
| 6,134,003 A | | 10/2000 | Tearney et al. | |
| 6,216,029 B1 | * | 4/2001 | Paltieli ........................ | 600/427 |
| 6,238,389 B1 | | 5/2001 | Paddock et al. | |
| 6,669,635 B2 | * | 12/2003 | Kessman et al. ........... | 600/437 |
| 6,695,786 B2 | * | 2/2004 | Wang et al. ................. | 600/461 |
| 6,755,789 B2 | * | 6/2004 | Stringer et al. ............. | 600/461 |
| 2003/0109833 A1 | | 6/2003 | Sharpe | |

\* cited by examiner

Primary Examiner—Francis J. Jaworski
(74) Attorney, Agent, or Firm—Ray F. Cox, Jr.

(57) ABSTRACT

A device to guide the placement of the catheter needle more accurately by placing the needle with a mechanical firing mechanism. The device is an integrated handheld unit comprising an ultrasonic probe with a miniature display and a mechanical firing mechanism that holds the catheter needle and deploys it into the target. The device is connected to an external ultrasound machine which provides the imaging for the device. The display provides a graphical user interface to assist in alignment with the target. The depth of placement of the catheter is set by moving a horizontal indicator over the target display using thumb switches on the handle of the device. The thumb switches are connected to a servo motor or the like that adjusts the angle at which the catheter is deployed. The servo motor simultaneously adjusts the distance of the catheter from the skin of the patient to compensate for the change in the length of the path to the target caused by the change in deployment angle. The catheter needle is deployed by a stored energy mechanism. The device may also include sensors to verify accurate placement of the catheter.

10 Claims, 2 Drawing Sheets

ULTRASONIC GUIDED CATHETER DEPLOYMENT SYSTEM

CROSS-REFERENCE TO RELATED APPLICATIONS

This application claims the benefit of U.S. Provisional Patent Application No. 60/389,432 filed Jun. 17, 2002, the disclosure of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to guiding devices to be used in conjunction with medical ultrasound devices, and in particular, to such guides for assisting in the placement of catheter needles or the like.

2. Brief Description of the Related Art

Ultrasound devices are commonly used in medical procedures to produce an image of a portion of the body being scanned by the device. The scan is a two dimensional sectional image. Ultrasound devices are often used in conjunction with the placement of catheter needles or the like. The ultrasound image serves to locate the targeted portion of the body, for example, a tumor, to assist in the placement of the catheter needle or the like in the target. To more accurate orient the catheter needle, guides that clip to the ultrasound probe are known. In these devices the needle is releasably held at a fixed angle and is deployed manually by the physician. These devices are exemplified by U.S. Pat. No. 5,235,987 and a commercially available device, the Site-Rite® Disposable Needle Guide. Similar devices are disclosed in U.S. Pat. Nos. 4,469,106; 5,758,650; 6,296,614; 6,361,499; and 4,497,325. Some of these patents disclose devices that are angularly adjustable. A more complicated device to position a medical instrument using ultrasound imaging is disclosed in U.S. Pat. No. 6,206,832, where the relationship between the target tissue is determined with respect to a reference plate having a plurality of apertures. The ultrasound imaging is used to determine which aperture to use to guide the instrument to the target tissue.

U.S. Pat. No. 6,264,665 discloses a system for ocular microsurgery in which surgical tools may be advanced or retracted by a mechanical system.

U.S. Pat. No. 5,572,999 discloses a method and apparatus using imaging processing to develop information about an anatomical feature and to position a surgical instrument relative to the anatomical feature. Various imaging devices may be used to provide information to a display. A surgeon or other user may use the information from the display to position or reposition instruments using, e.g., a joystick.

U.S. Pat. No. 6,374,132 discloses a therapeutic system guided by information from an MRI device.

U.S. Pat. No. 6,216,029 disclose a method for free-hand guiding of a needle towards a target located in a patient's body. Devices are provided for sensing the position of both the ultrasound transducer and the needle. The position information is displayed on a screen to a user who may then direct the needle freehand to the target.

U.S. Pat. No. 5,704,791 discloses a virtual surgery system which provides a simulation based on image data. A surgical procedure may be simulated with the surgeon using a joystick or the like to navigate through the image.

U.S. Pat. No. 5,829,439 discloses a needle-like ultrasound probe. The probe comprises an inner needle received in a hollow outer needle. The inner needle is inserted into the patient by a drive mechanism that rotates and translates the inner needle to scan the imaged area.

U.S. Pat. No. 5,095,910 discloses a system for imaging a biopsy needle where the tip of the needle is vibrated and the resulting Doppler response is detected and used to locate the tip of the catheter.

References mentioned in this background section are not admitted to be prior art with respect to the present invention.

The limitations of the prior art are overcome by the present invention as described below.

BRIEF SUMMARY OF THE INVENTION

The present invention is a device to accurately place catheters into a targeted anatomical feature, such as a vein, an artery, or a tumor using ultrasonic imaging for guidance. As exemplified by U.S. Pat. No. 5,235,987 to Wolfe, prior art devices aid in the placement of a catheter needle by utilizing a guide that clips onto the ultrasonic probe. The guide engages the needle at a pre-set angle so that once the probe has identified the target, the needle may be manually deployed to enter the target.

The present invention is designed to guide the placement of the catheter needle more accurately by replacing the manual placement of the needle with a mechanical firing mechanism. The device is an integrated handheld unit comprising an ultrasonic probe with a miniature display and a mechanical firing mechanism that holds the catheter needle and deploys it into the target. The device is connected to an external ultrasound machine which provides the imaging for the device.

The display provides a graphical user interface to assist in alignment with the target. The probe is moved over the target site until the target is centered on the display horizontally. The depth of placement of the catheter is set by moving a horizontal indicator over the target display using thumb switches on the handle of the device. The thumb switches are connected to a servo motor or the like that adjusts the angle at which the catheter is deployed. The servo motor simultaneously adjusts the distance of the catheter from the skin of the patient to compensate for the change in the length of the path to the target caused by the change in deployment angle.

Once the target is centered on the display and the deployment depth is set, the catheter is deployed by the operator triggering a stored energy mechanism, such as a spring or hydraulics.

The device may also include sensors to verify accurate placement of the catheter. A tracking mechanism could include an electro-optic system where a reflector is attached to the catheter housing. A light source place on the base of the device and aimed at the reflector can be used to detect the position of the catheter and through feedback control accurately align the catheter despite errors in the mechanism.

It is therefore an object of the present invention to provide for a guide for an catheter needle wherein the needle is inserted mechanically rather than manually.

It is a further object of the present invention to provide for a catheter needle guide having a display to assist in positioning the needle and mechanical means used in conjunction with the display to position the needle at the correct angle to intersect the target tissue.

It is also an object of the present invention to provide for a needle guide having sensors to verify the correct place ment of the catheter needle, such as an electro-optic system with a reflector attached to the catheter and a suitable optical imaging system.

These and other features, objects and advantages of the present invention will become better understood from a consideration of the following detailed description of the preferred embodiments and appended claims in conjunction with the drawings as described following:

DETAILED DESCRIPTION OF THE INVENTION

Figure 1:
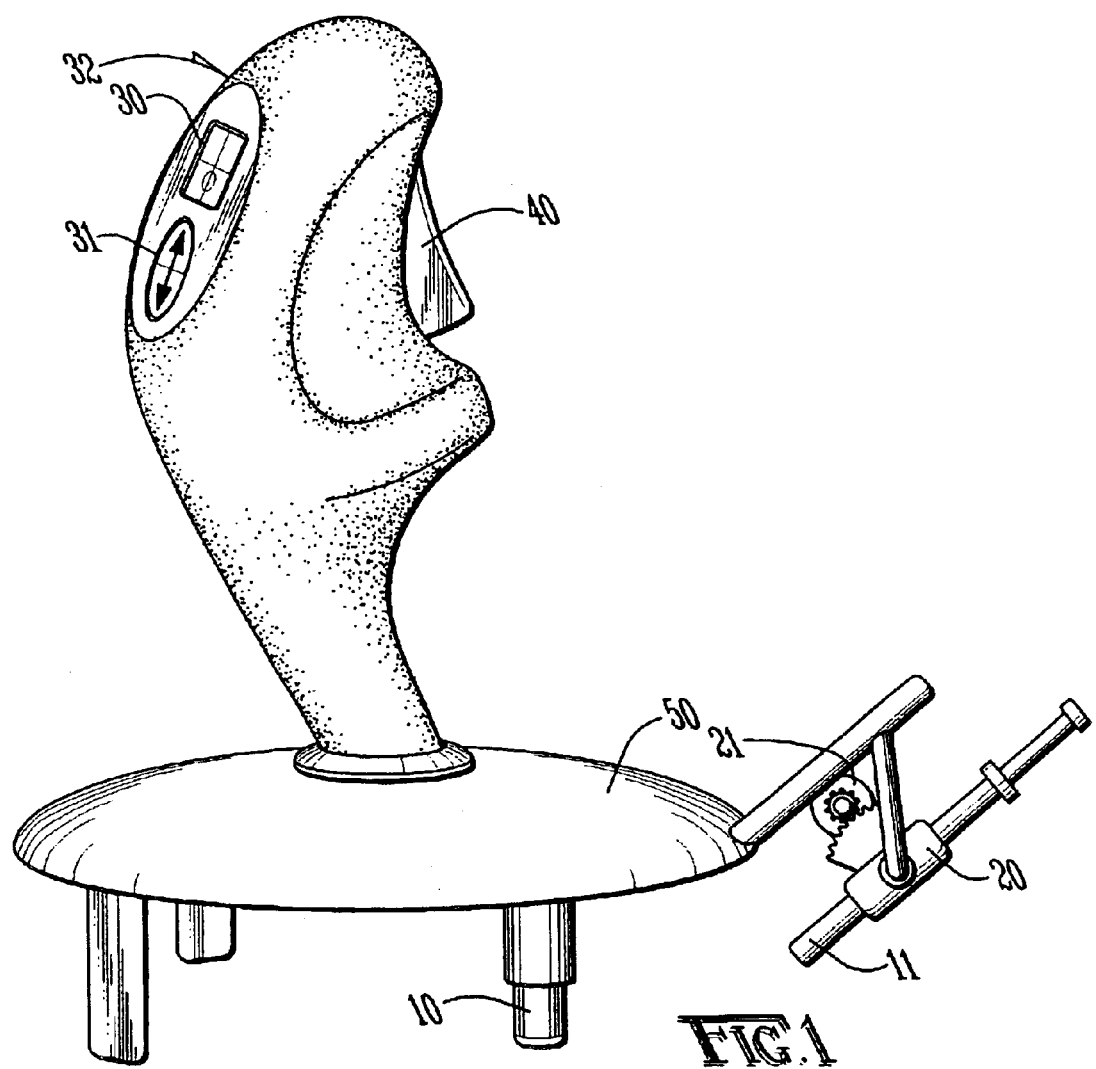
FIG. 1 is a side elevation view of the device.
Figure 2:
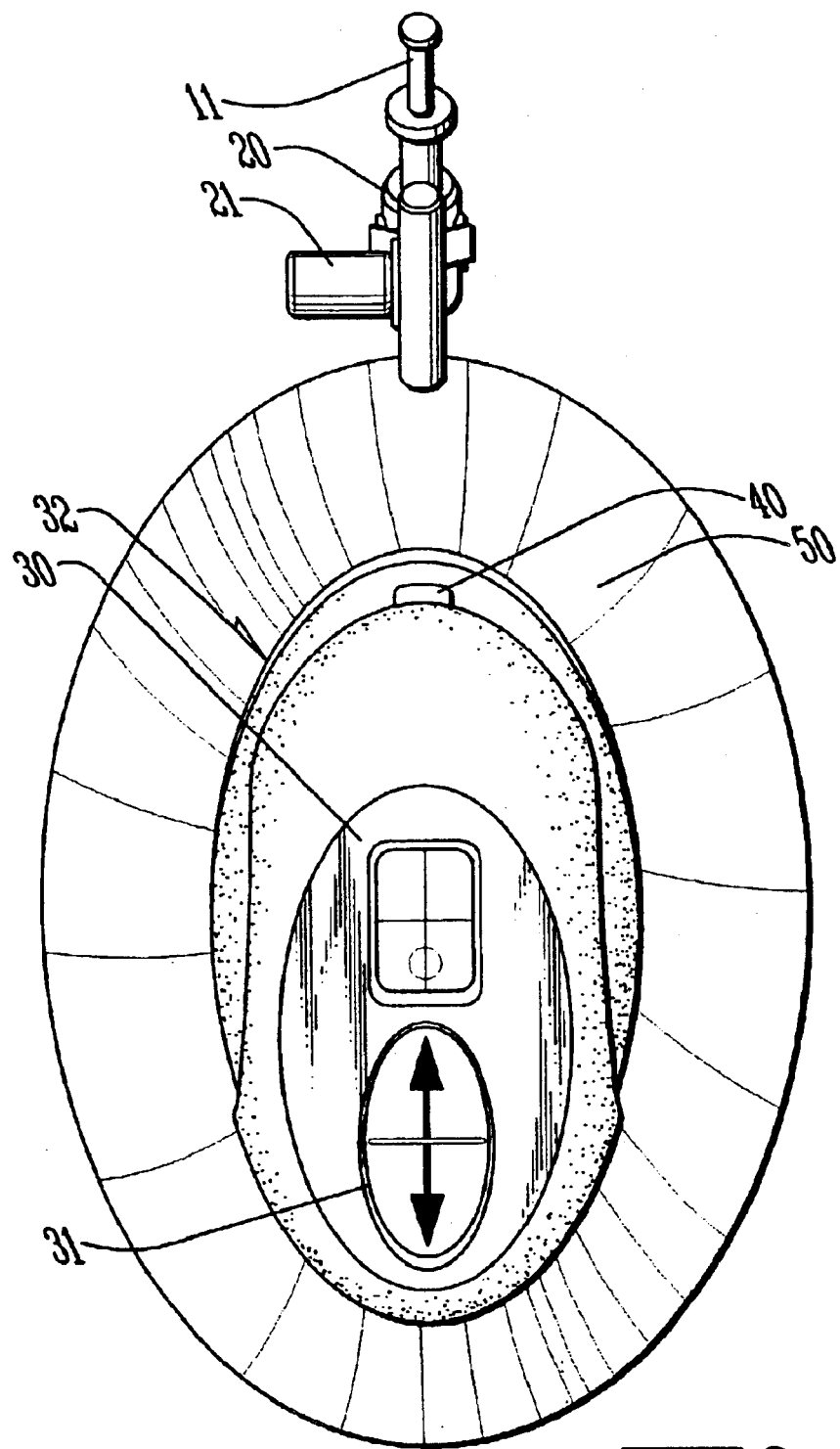
FIG. 2 is a view of the graphical user interface from the perspective of the user.

With reference to FIGS. 1 and 2, the preferred embodiment of the present invention is described. The present invention is a device to accurately place a catheter needle 11 into targeted anatomical regions, such as veins, arteries and tumors, using ultrasonic imaging for guidance. The device comprises an ultrasonic probe 10, a mechanical firing mechanism 20, and a miniature display 30 integrated to form a single, hand-held system. The device is connected to an external ultrasound machine (not shown) that provides the imaging for the miniature display 30.

The miniature display 30 also serves as a graphical user interface that provides alignment information. The device is moved over the target site until the target is centered on the display 30 horizontally. A fixed vertical indicator on the display 30 aids in determining that the target is bisected horizontally. Depth of placement of the catheter 11 is set by moving a horizontal indicator over the displayed target using up and down thumb switches 31 on the handle 32 of the device until the target is bisected vertically by the horizontal indicator. The thumb switches 31 are connected to a servo motor 21, or comparable mechanism, that adjusts the catheter deployment angle. Simultaneously, the distance of the catheter 11 from the skin of the patient is adjusted to compensate for the change in path length caused by the change in deployment angle. The combination of these two motions causes the travel of the catheter 11 to terminate at the plane indicated by the vertical indicator of the graphical user interface 30 at a given target depth, i.e., where the horizontal and vertical indicators cross.

Information regarding the deployment angle of the needle may be obtained using an encoder. Such an encoder could, for example, be the type of mechanism found in a computer mouse, or other types of angular encoders.

Once the user superimposes the crossed horizontal and vertical indicators over the target, a trigger 40 is tripped and the catheter 11 is rapidly discharged by the firing mechanism 20 using stored energy, such as a spring, hydraulics or the like.

Sensors may be incorporated into the device to verify accurate vectoring. The image stability can also be monitored to prevent deployment should unexpected dynamic conditions arise.

The movement of the catheter 11 is monitored with a tracking system to ensure that the catheter 11 is positioned at the correct angle and distance from the target as determined by the ultrasonic system. This avoids any errors due to thermal drift, backlashes and wear in the driving mechanism that can affect the aiming procedure. In one embodiment, a tracking system comprises an electro-optic system where a mirror or reflection surface is attached to or made part of the catheter housing. A light source, e.g., a laser light emitting diode, is placed on the base 50 of the device and aimed at the reflection surface on the catheter housing. Thus, any small movement of the catheter 11 will change the angle of reflection of the laser beam, which will be detected by an optical detector on the base 50 allowing the catheter position to be measured and controlled precisely. The tracking system acts as feedback control to accurately align the catheter to the position needed to deploy the catheter to desirably within 0.2 mm. Once the catheter 11 is deployed the movement of the catheter 11 is terminated by a mechanical stopper. To avoid additional movements of the catheter 11, a locking mechanism, such as an electromagnet holds the shaft firmly in its deployed position. After deployment, the shaft can be released to pull the catheter 11 out.

To further assure stability of the system, once the target is located, the device can be held in position with an external holding feature and the operator can move the catheter until the catheter is in position, i.e., with the horizontal and vertical indicators on the target.

The present invention takes advantage of predictable mechanical motion to ease the difficulty associated with accurate catheter placement. Current technology provides a guide to set the catheter at the appropriate angle and requires the user to monitor the ultrasound display to monitor a dynamic process. The present invention terminates in a region defined by the user allowing dramatic improvement of "first stick." The device should allow less experienced staff to achieve results comparable to more experienced staff.

While the preferred embodiments of the present invention have been described with reference to an external ultrasound machine, a less expensive sensor array may be used with the present invention as a stand alone embodiment. While such a sensor array might have lower resolution imaging, it would provide adequate information for targeting purposes. The information may be digitally processed and presented on the display in place of the real time image from an ultrasound machine. The image may be enhanced with pattern recognition software. Image processing, position decoding and display electronics may be implemented on, or provided in conjunction with, a microprocessor.

The present invention has been described with reference to certain preferred and alternative embodiments that are intended to be exemplary only and not limiting to the full scope of the present invention as set forth in the appended claims.

What is claimed is:

1. A device used in conjunction with an external ultrasound machine providing imaging information to guide the placement of a catheter needle into a targeted anatomical feature, comprising:

an ultrasonic probe and means for operatively connecting said ultrasonic probe to the external ultrasound machine;

receiving means for receiving the imaging information from the external ultrasound machine;

displaying means integral with said ultrasonic probe for displaying the imaging information from the external ultrasound machine;

means associated with said displaying means for graphically indicating a depth to the targeted anatomical feature;

mechanical means for deploying the catheter needle into the anatomical feature; and means for holding the catheter needle at an angle and distance from the anatomical feature so as to deploy the catheter needle into the anatomical feature at the indicated depth.

2. The device of claim 1 wherein said means for indicating a depth to the targeted anatomical feature comprises an horizontal indicator on said display means and manual means for moving said horizontal indicator to coincide with said depth on said display means.

3. The device of claim 2 wherein said means for holding the catheter further comprises servo-mechanical means for adjusting said angle and distance of the catheter needle in response to said manual means for moving said horizontal indicator.

4. The device of claim 3 wherein said manual means for moving said horizontal indicator comprises at least one thumb switch.

5. The device of claim 4 wherein said mechanical means for deploying the catheter needle comprises a stored energy mechanism.

6. The device of claim 5 wherein said stored energy mechanism comprises a hydraulic mechanism.

7. The device of claim 5 wherein said stored energy mechanism comprises a spring mechanism.

8. The device of claim 1 further comprising means for verifying placement of the catheter into the targeted anatomical feature.

9. The device of claim 8 wherein said means for verifying placement of the catheter comprises a reflector attached to the catheter housing, a light source aimed at said reflector and electro-optic means for detecting the position of the reflector.

10. The device of claim 9 further comprising feedback means for aligning the catheter based on the position detected by said electro-optic means.

* * * * *